(12) United States Patent
Brusasco et al.

(10) Patent No.: US 7,307,264 B2
(45) Date of Patent: Dec. 11, 2007

(54) APPARATUS FOR IRRADIATING A TARGET VOLUME

(75) Inventors: Caterina Brusasco, Bossiere (BE); Bruno Marchand, Nivelles (BE); Jean-François De Le Hoye, Couture-St-Germain (BE); Damien Prieels, Brussels (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 275 days.

(21) Appl. No.: 10/513,544

(22) PCT Filed: Nov. 29, 2002

(86) PCT No.: PCT/BE02/00180

§ 371 (c)(1),
(2), (4) Date: May 23, 2005

(87) PCT Pub. No.: WO03/101538

PCT Pub. Date: Dec. 11, 2003

(65) Prior Publication Data

US 2005/0238134 A1 Oct. 27, 2005

(30) Foreign Application Priority Data

May 31, 2002 (EP) ................................. 02447101

(51) Int. Cl.
*H01J 33/02* (2006.01)
(52) U.S. Cl. .............................. 250/492.22; 250/492.3; 250/397
(58) Field of Classification Search ................ 430/296, 430/30, 312; 250/492.2, 492.22
See application file for complete search history.

(56) References Cited

U.S. PATENT DOCUMENTS

| | | | |
|---|---|---|---|
| 4,654,531 A | 3/1987 | Morris et al. | |
| 5,017,789 A | 5/1991 | Young et al. | |
| 5,596,201 A | 1/1997 | Charpak | |
| 6,717,162 B1 * | 4/2004 | Jongen | 250/505.1 |
| 2004/0155206 A1 * | 8/2004 | Marchand et al. | 250/492.3 |

FOREIGN PATENT DOCUMENTS

DE 37 44 808 A1 9/1989

(Continued)

OTHER PUBLICATIONS

Chu et al. "Instrumentation for treatment of cancer using proton and light-ion beams". *Review of Scientific Instruments* vol. 64, No. 8, pp. 2055-2122, 1993.

*Primary Examiner*—Nikita Wells
*Assistant Examiner*—Johnnie L Smith, II
(74) *Attorney, Agent, or Firm*—Fitch, Even, Tabin & Flannery

(57) ABSTRACT

An irradiation apparatus for irradiating by scanning a target volume according to a predetermined dose profile with a scanning beam of charged particles forming an irradiation spot on said target volume, said apparatus comprising:
a beam generating device,
a reference generator for computing, from said predetermined dose profile, through a dynamic inverse control strategy, the time evolution of commanded variables, these variables being the beam current I(t), the spot position settings x(t),y(t) and the scanning speed settings $v_x(t)$, $v_y(t)$,
a monitor device having means for detecting at each time (t), the actual spot position as a measured position defined by the values $x_m(t), y_m(t)$ on the target volume, characterised in that said irradiation apparatus further comprises means for determining the differences $e_x(t)$, $e_y(t)$ between the measured values $x_m(t)$, $y_m(t)$ and the spot position settings x(t) and y(t), and means for applying a correction to the scanning speed settings $v_x(t)$ and $v_y(t)$ depending on said differences $e_x(t)$, $e_y(t)$. The present invention is also related to a monitor for determining beam position in real-time.

5 Claims, 6 Drawing Sheets

FOREIGN PATENT DOCUMENTS

| | | |
|---|---|---|
| EP | 0 282 665 | 3/1987 |
| EP | 0 986 070 A1 | 9/1998 |
| EP | 1 045 399 A1 | 4/1999 |
| FR | 2 602 058 | 7/1986 |
| WO | 00/40064 | 7/2000 |

* cited by examiner

APPARATUS FOR IRRADIATING A TARGET VOLUME

FIELD OF THE INVENTION

The present invention is related to an apparatus for irradiating a target volume with a beam of charged particles such as protons or heavy ions and to a method for implementing said apparatus.

The present invention is also related to an apparatus for monitoring said beam.

A possible application of such apparatus is for the treatment of tumors in patients.

STATE OF THE ART

Many types of irradiation systems are used for the treatment of tumors in patients. It is important to precisely deliver the required dose to the tumor region, and as little dose as possible to the environing healthy tissues. It has been known to use X-rays or gamma rays for this purpose. High-energy electrons have also been used. However, heavier charged particles have the property that they deposit energy in matter according to the so-called "Bragg-peak", i.e. a dose-depth curve having a plateau, a peak, and a sharp fall-off beyond the peak. The height of the peak corresponding to the depth of penetration of the beam in the tissues depends on energy. It is therefore possible to direct a beam to a precise volume in a patient.

Many techniques have been devised for delivering the dose according to a required pattern. The double scattering method combines the use of a first and a second scatterers for producing a beam having a width larger than the tumor to be treated, and a collimator for delimiting the beam to the exact tumor shape (CHU W. T. et al.:"Instrumentation for treatment of cancer using proton and light-ion beams" Rev.Sci. Instrum. 64(8), August 1993, pages 2080-2081).

In the so-called "voxel scanning method", the target volume is divided in volume elements called "voxels". The beam is directed to a first voxel, and when the prescribed dose is reached, the irradiation is stopped by diverting the beam in another direction with a fast kicker magnet. A sweeper magnet is then instructed to direct the beam to a next voxel, and the irradiation of this voxel is performed (PEDRONI E. et al.: "200 MeV proton therapy project at the Paul Scherrer Institute: Conceptual design and practical realization", Med. Phys. 22(1), January 1995, pages 39-42).

The international application WO00/40064 in the name of the applicant discloses an improved technique, called "Pencil Beam Scanning" (hereafter named PBS) wherein the beam is not interrupted between the irradiation of successive individual voxels. Said method will be described hereafter in details. In the PBS method, as shown on FIG. 1, the beam is moved continuously along a path, by scanning magnets in the x and y directions. The target volume is irradiated layer by layer. With a simultaneous modulation of the beam spot speeds and variation of beam current, one can obtain any dose distribution on a scanned slice and an excellent mapping of the delivered dose to the target volume. Both the voxel scanning method and the PBS method can perform a 3D conformal irradiation.

In the PBS method, as shown on FIG. 2, the therapist uses a treatment planning system for obtaining a dose map D(x,y,z) giving, for each point (x,y,z) in the target, the value of the required dose. From this dose map, a reference generator computes the trajectories, giving, for each depth z, the required speeds $v_x(t)$, $v_y(t)$ and current I(t) of the pencil beam, as a function of time t. The word "trajectory" is used here in the sense used in control theory, i.e. the time dependence of a commanded variable. The $v_x(t)$ and $v_y(t)$ signals are used to drive the x and y scanning magnets. A first inner control loop ensures that the magnets receive the correct control output from the scanning magnet power supply (SMPS) derived from the reference generator calculation. The beam current setpoint I(t) is used to drive the Ion Source Electronic Unit (ISEU), feeding the Ions source arc power supply (Arc PS). A second inner control loop ensures that the measured beam current is according to the requirement. The beam current is measured by an ionisation chamber in the beam line.

When the beam traverses matter, a scattering occurs, and the width of the beam is increased. For PBS, it is necessary that the beam be as narrow as possible.

In the above scheme, however, no certainty is given that the actual dose applied is equal to the required dose map. Many sources of noise, drift and errors may result in a discrepancy between actual and required dose. Moreover, for safety reasons, it is of the utmost importance that, in case of equipment failure, the irradiation apparatus reacts safely. Means for monitoring beam position and current in real-time, with good precision, over a large area, and that do not increase the beam width, and thereby allowing a fast control, have heretofore not been available.

AIMS OF THE INVENTION

The present invention aims to provide a PBS irradiation apparatus wherein the difference between the actual and required dose is minimised.

Another aim of the present invention is to provide an apparatus having an improved safety, in case of equipment failure.

The present invention also aims to provide an irradiation apparatus having means for monitoring the beam position and current in a precise and rapid way, and that do not increase the beam width.

In particular, the present invention aims to provide an irradiation apparatus and process, which allow optimal 3d conformation of the dose, with improved precision and safety.

SUMMARY OF THE INVENTION

A first object of the present invention is related to an irradiation apparatus for irradiating by scanning a target volume according to a predetermined dose profile with a scanning beam of charged particles forming an irradiation spot on said target volume, said apparatus comprising:

a beam generating device, a reference generator for computing, from said predetermined dose profile, through a dynamic inverse control strategy, the time evolution of commanded variables, these variables being the beam current I(t), the spot position settings x(t),y(t) and the scanning speed settings $v_x(t)$, $v_y(t)$, a monitor device having means for detecting at each time (t), the actual spot position as a measured position defined by the values $x_m(t), y_m(t)$ on the target volume, characterised in that said irradiation apparatus further comprises means for determining the differences $e_x(t)$, $e_y(t)$ between the measured spot values $x_m(t)$, $y_m(t)$ and the spot position settings x(t) and y(t), and means for applying a correction to the scanning speed settings $v_x(t)$ and $v_y(t)$ depending on said differences $e_x(t)$, $e_y(t)$.

Preferably, the monitor device further comprises means for measuring the total instantaneous dose deposited by the beam in the target volume, and means for correcting this dose deposition or for pausing the beam and informing an external operator when said instantaneous dose is outside of an expected range. The term "total instantaneous dose" refers to the dose deposited in a short time interval (of the order of 100 microseconds) during the scanning. It is proportional to the instantaneous beam current divided by the scanning speed.

Preferably, the irradiation apparatus according to the present invention is arranged so as to generate a beam in one direction and so as to irradiate with said beam the target volume in layers perpendicular to said direction, said layers being irradiated in one or more irradiation frames, said apparatus being characterised in that the monitor device comprises in addition means for determining the dose distribution in a plane perpendicular to the beam direction, for each successive irradiation frame, and means for pausing the beam and informing the external operator when said dose distribution is outside of an expected range.

A second object of the present invention is related to an apparatus for monitoring a beam of charged particles comprising:

a first ionisation chamber with an anode and a corresponding cathode, said chamber having a set of parallel conducting strips on the anode, and a conducting surface on the cathode, and a gas gap in between, a second ionisation chamber with an anode and a corresponding cathode, said chamber having a set of parallel conducting strips on said anode, and a conducting surface on said corresponding cathode, and a gas gap in between, the strips of the second ionisation chamber being orthogonal to the strips of the first ionisation chamber.

The apparatus for monitoring the beam may also comprise a third ionisation chamber having an integral anode and an integral corresponding cathode, and a fourth ionisation chamber having an anode, said anode being made of an array of pads, and a corresponding cathode.

In said ionisation chambers, the gap between the anode and the corresponding cathode is preferably comprised between 3 mm and 15 mm.

In addition, in said ionisation chambers, the electric field between the plates defining the anode and the cathode may be comprised between 1 and 8 kV/cm.

Preferably, the gap in the first and second ionisation chambers is 5 mm, the electric field in said ionisation chambers is 2 kV/cm or higher, while the gap in the third ionisation chamber is 10 mm, and the electric field in said third chamber is 4 kV/cm or higher.

The invention is also related to a process for irradiation of a target volume with a beam of charged particles forming an irradiation spot on said target volume, said process comprising the steps of determining a dose distribution profile referenced as a map $D(x,y,z)$;

determining, from said dose map, trajectories comprising spot position settings $x(t)$, $y(t)$, scanning speed settings $v_x(t)$, $v_y(t)$ and a beam current setting $I(t)$ for a set of irradiation depths z;

feeding said scanning speed signals $v_x(t)$ and $v_y(t)$ to a scanning magnet system;

feeding said beam current signal $I(t)$ to a beam generating device;

detecting and measuring the actual spot values $x_m(t)$, $y_m(t)$, determining the differences $e_x(t)$, $e_y(t)$ between said measured spot values $x_m(t)$, $y_m(t)$ and the spot position settings $x(t)$ and $y(t)$; and applying a correction to the scanning speed settings $v_x(t)$ and $v_y(t)$ depending on said differences $e_x(t)$, $e_y(t)$.

Finally, the invention is also related to the use of said irradiation apparatus or process for irradiating a target.

SHORT DESCRIPTION OF THE DRAWINGS

DESCRIPTION OF A PREFERRED EMBODIMENT OF THE INVENTION

Figure 3:
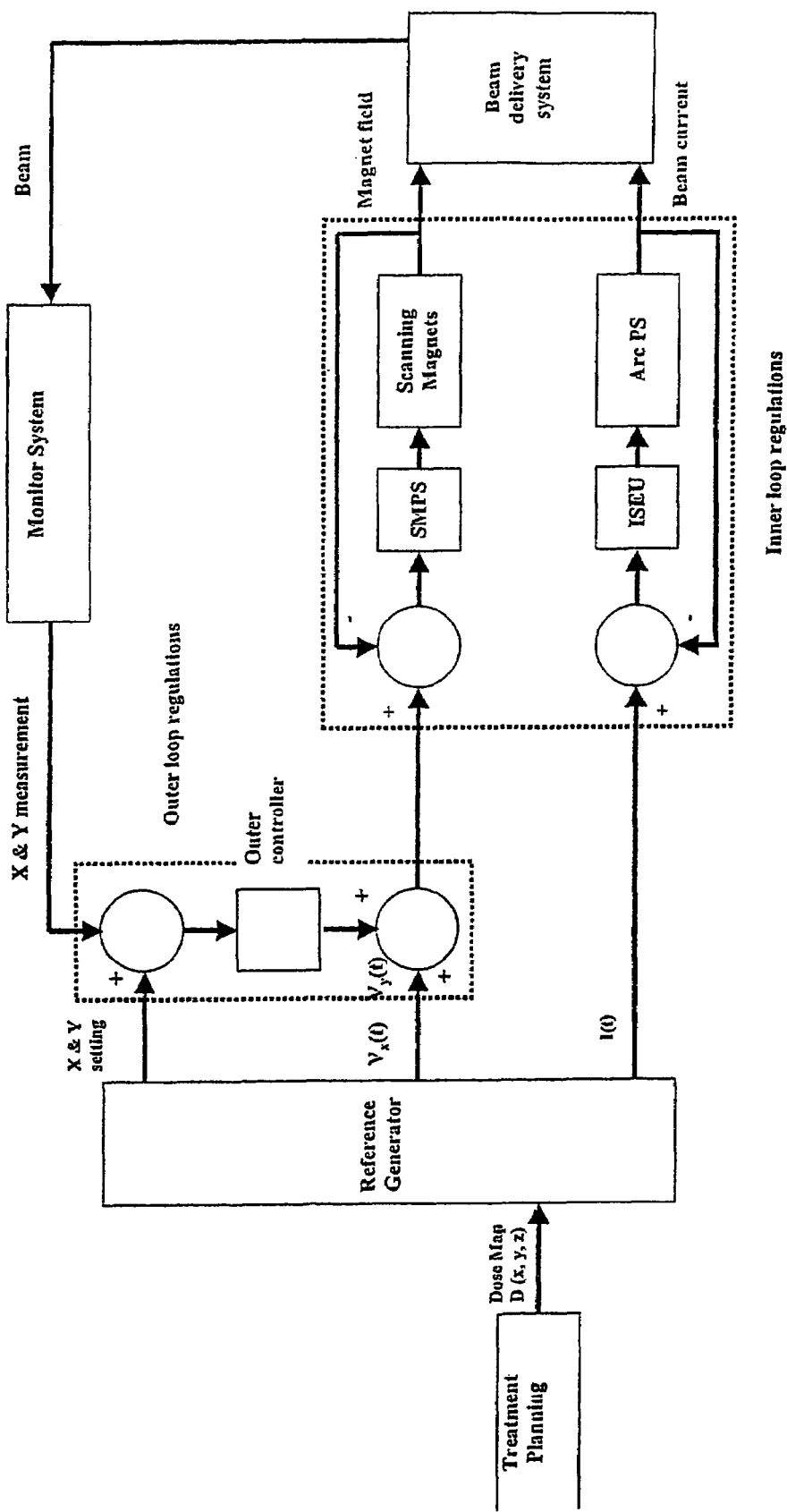
FIG. 3 is a block diagram of the control signals involved in the working of a PBS irradiation apparatus according to the invention.

A first embodiment of the present invention is illustrated on FIG. 3.

Using the treatment planning system, the therapist generates a dose map $D(x,y,z)$ representing the dose for each point x,y,z in the target. The reference generator computes the trajectories, comprising the required speed $v_x(t)$, $v_y(t)$, the required beam current $I(t)$, and, in addition, the required position $x(t)$, $y(t)$. The speed data are sent to a scanning magnet power supply (SMPS). The coil of a scanning magnet being, in first approximation, a pure inductance, the current through the coil is proportional to the time integral of the applied voltage. The displacement of the beam is proportional to the field, and hence to the current. Therefore, by applying to the coils of the scanning magnets a voltage proportional to the required speed $v_x(t)$ or $v_y(t)$, one obtains the required beam spot speed.

According to the invention, an outer control loop for controlling the dose comprises the following elements: a monitor device performs the function of determining the x and y position of the beam, at a sampling rate of 5 to 10 kHz. This is performed by two orthogonal strip planes. The strips are 0.6 cm wide. The first strip plane comprises 38 strips, and the second strip plane comprises 48 strips, in a direction orthogonal to the first strips. Due to the gaussian-like shape of the beam, one can reconstruct the mean position x, y of the beam with a precision better than a fraction of a mm, by applying the speed correction as described hereafter. These measured values are subtracted from the required positions given by the reference generator. The differences are fed into a soft gain controller, which may be a classical PID controller, and the output of it is added, as a correction, to the required speeds $v_x(t)$, and $v_y(t)$. This selection of acquisition resolution and frequency is attainable with the monitor described hereafter, and allows the outer control loop to correct efficiently any discrepancy between the required and actual dose.

The strip ionisation chambers acquire the charge collected for each of the strips at a rate of 10 kHz. The acquired position of the beam may be determined by computing the centroid of the set of acquired values. This would give an excellent precision if the beam were static, or moving slowly with respect to the acquisition period. However, at a speed of 20 m/s, the beam moves 2 mm during the 100 μs acquisition period, giving a too large error. Therefore, a speed correction is applied by (i) determining the instantaneous beam speed in the successive acquired positions, and (ii) applying a position correction on the actual position, corresponding to the displacement as calculated from the instantaneous beam speed. This achieves the above-quoted precision.

Figure 1:
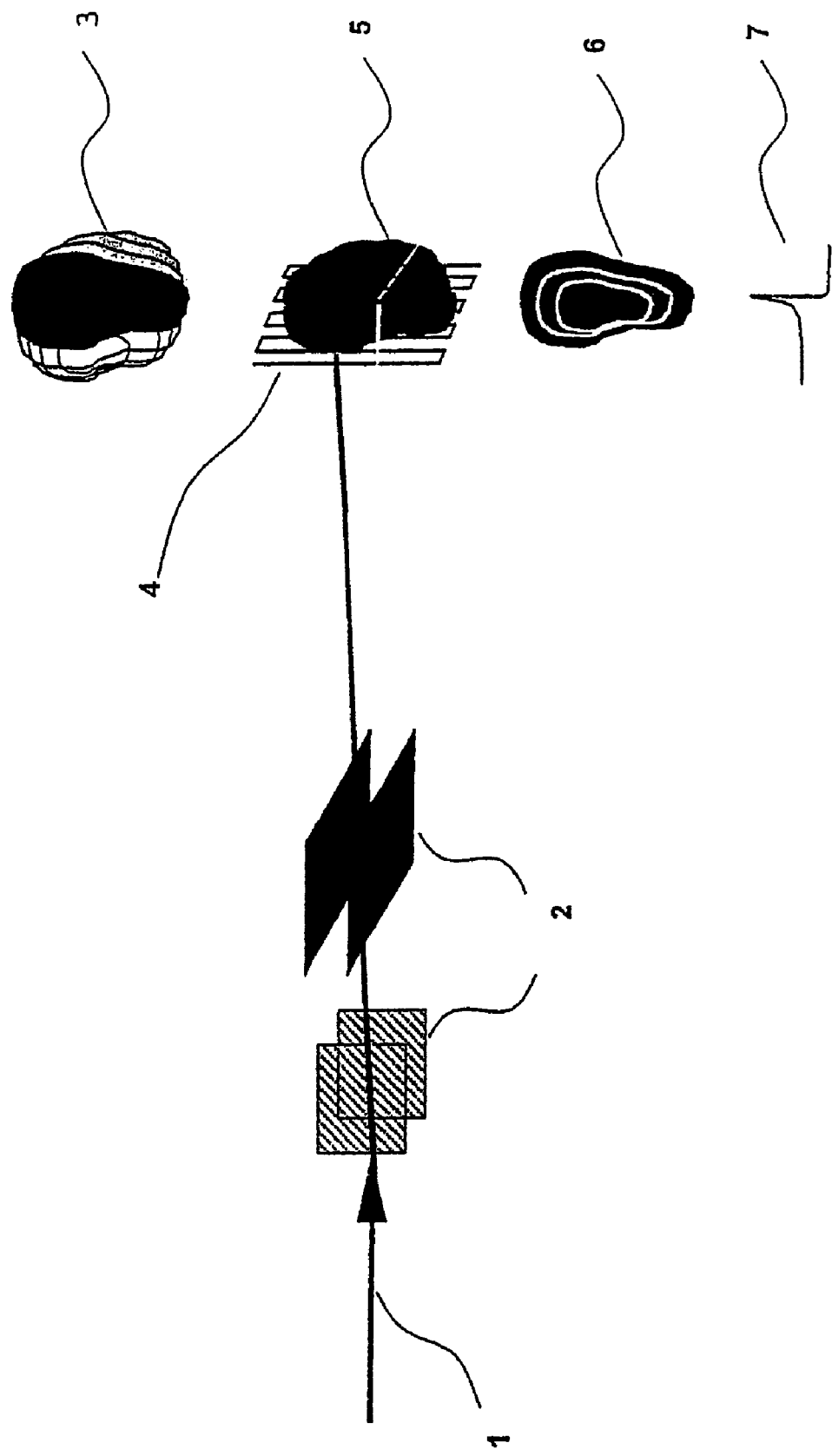
FIG. 1 is a general schematic representation of a PBS irradiation apparatus according to the prior art or according to the invention.
Figure 2:
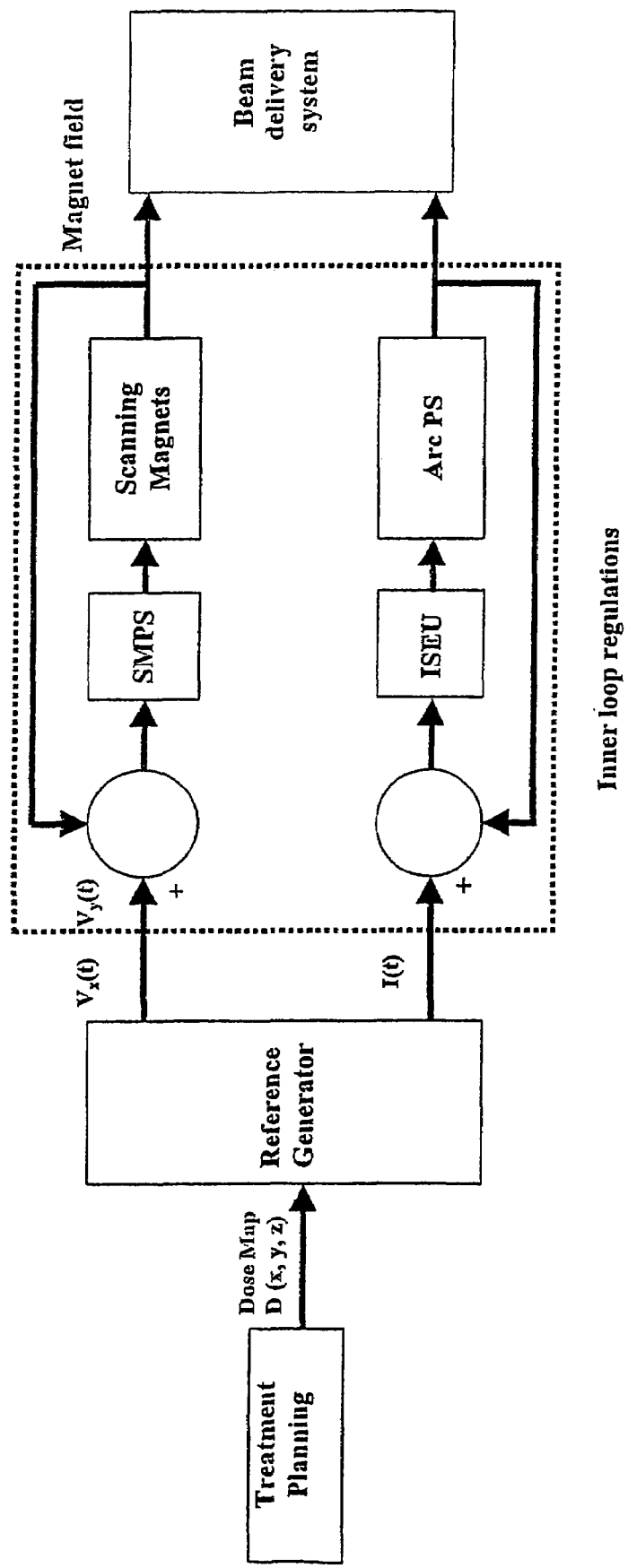
FIG. 2 is a block diagram of the control signals involved in the working of a PBS irradiation apparatus according to the prior art.

Referring to FIG. 1, the beam is scanned with a regular pattern over a transversal area of the target with a beam spot characterized by a gaussian fluence distribution with a sigma at isocenter in air variable from 2 to 10 mm. The beam spot moves with a maximum velocity of 20 m/s along the x direction and of 2 m/s in the y direction over a maximum area of 40×30 cm$^2$ at isocenter. Thanks to the high scanning speed, the total dose in every plane is released by means of several subsequent scanning frames of the target area, each scanning frame corresponding to the deposition of a few percent of the total dose. A dose deposition of 0.04 Gy is chosen as the instantaneous maximum of the dose distribution in one scanned line, corresponding to 2% of a total dose of 2 Gy. This way, the number of scannings will be different for the different target slabs, but the dose-rate and therefore the beam current will remain within a limited range on the whole target volume.

Figure 4:
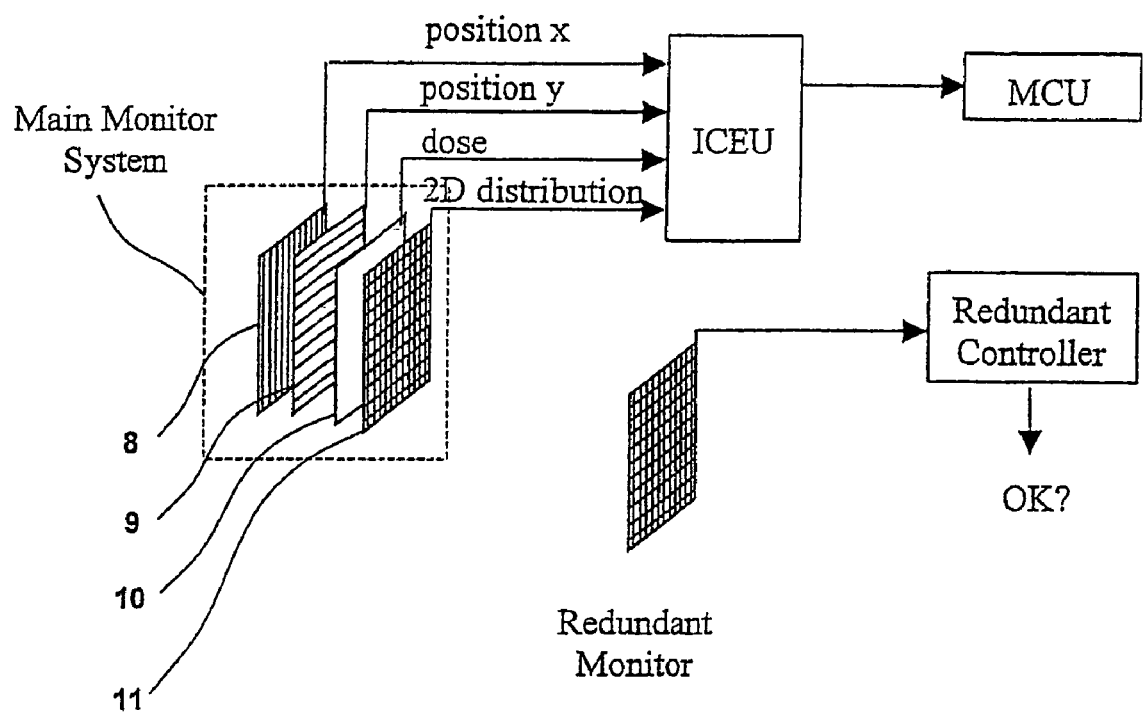
FIG. 4 is a schematic drawing of a beam monitor for an irradiation apparatus according to the invention.

Referring to FIG. 4, the monitor comprises a set of successive ionisation chambers. The general principle of an ionisation chamber is as follows: A high voltage is applied between two parallel electrodes. A gas (here air or nitrogen) between the plates is ionised by the beam passing perpendicularly to the planes. As a result of the electric field, the ions are collected on the electrodes, and the charge can be measured. As the creation of one electron-ion pair requires a known average energy, depending on the gas and on the irradiation type, the collected charge is directly proportional to the energy deposited in the gas. A recycling integrator circuit provides a 16-bit counter proportional to the detected charge. The recycling integrator was developed as a 0.8 μm CMOS technology chip (TERA06) by INFN (Istituto Nazionale di Fisica Nucleare, Torino). Each of these chips provides 64 channels. The minimum detectable charge is adjustable between 50 fC and 800 fC, and the read rate in the linear region can be as high as 5 MHz. The values provided by the counters are sent to an Ionisation Chamber Electronic Unit (ICEU) and the processed data are used by the Master Control Unit (MCU) of the irradiation apparatus for performing the control, safety and operator interface functions. A redundant pad chamber performs a redundant check, for improving safety.

As described above, the monitor comprises two strip planes. In addition to these strip planes, the monitor may comprise an integral plane, measuring the instantaneous beam current, and hence the total instantaneous dose. This data is acquired at the same rate as the strip data.

The monitor also comprises a plane made of individual square pads. The pads have a size of 0.7 cm×0.7 cm.

Figure 5:
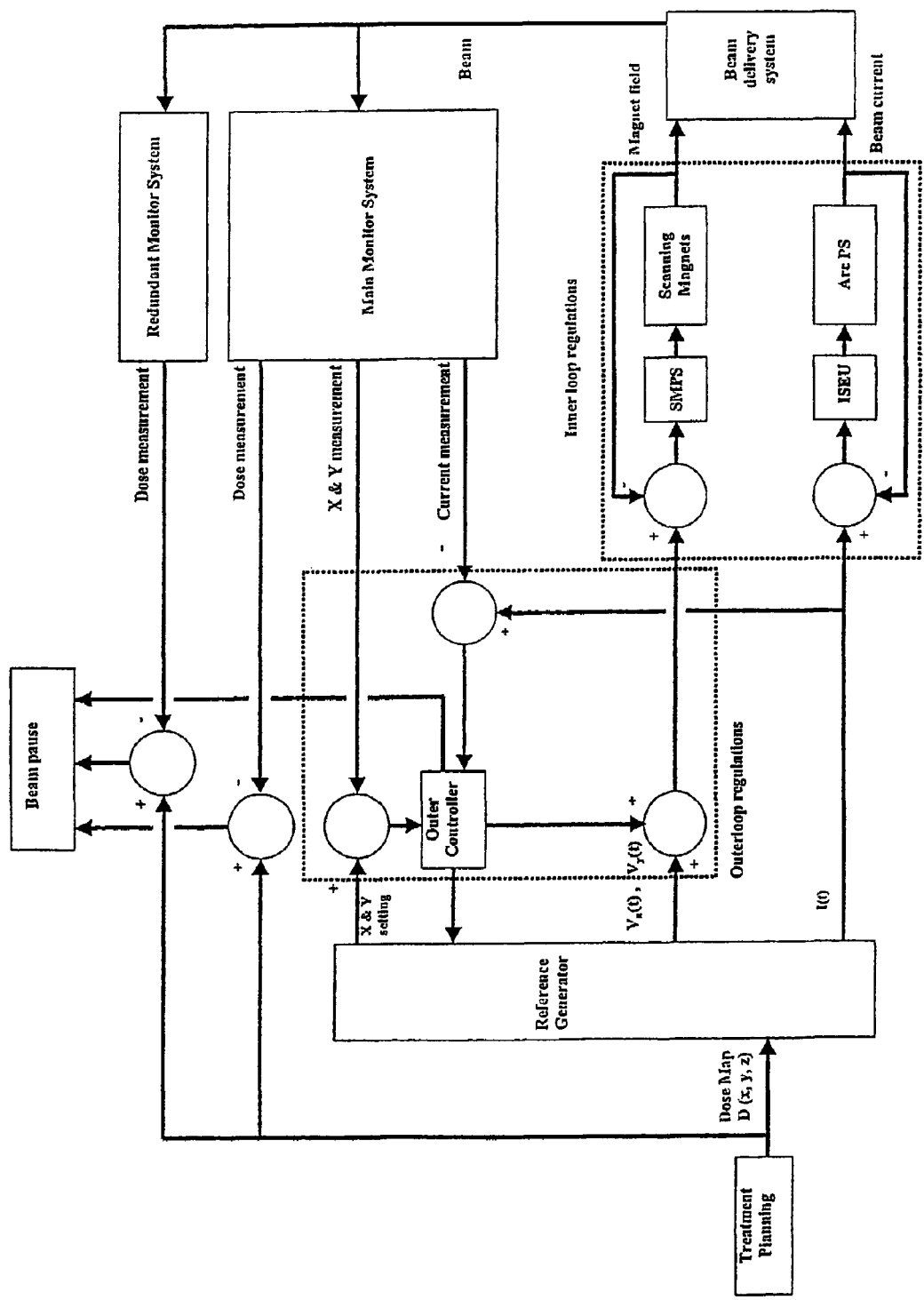
FIG. 5 is a block diagram of the control signals involved in the working of a PBS irradiation apparatus according to a preferred embodiment of the invention.

FIG. 5 shows a preferred embodiment of the invention. In this embodiment, the monitor performs two additional measurements, and additional control functions are based thereon. The first additional measurement is the measurement of the instantaneous beam current. This measurement is compared with the required value, and the resulting error is fed into the outer controller for improving the correction to speed settings. The outer controller also performs the function of pausing the beam (i.e. stop any irradiation) in case the error is larger than an acceptable level. This realises a first level of safety. The outer controller can also provide an input to the reference generator for modifying the trajectory calculation. The second additional measurement is the 2D dose map, as measured by the pad plane. These are compared, at a rate up to 20 Hz, with the dose map, and can cause a beam pause in case of large error. This provides a second level of safety. A third safety is provided by the use of a redundant pad monitor, performing, in parallel, the same function as the primary pad plane.

Figure 6:
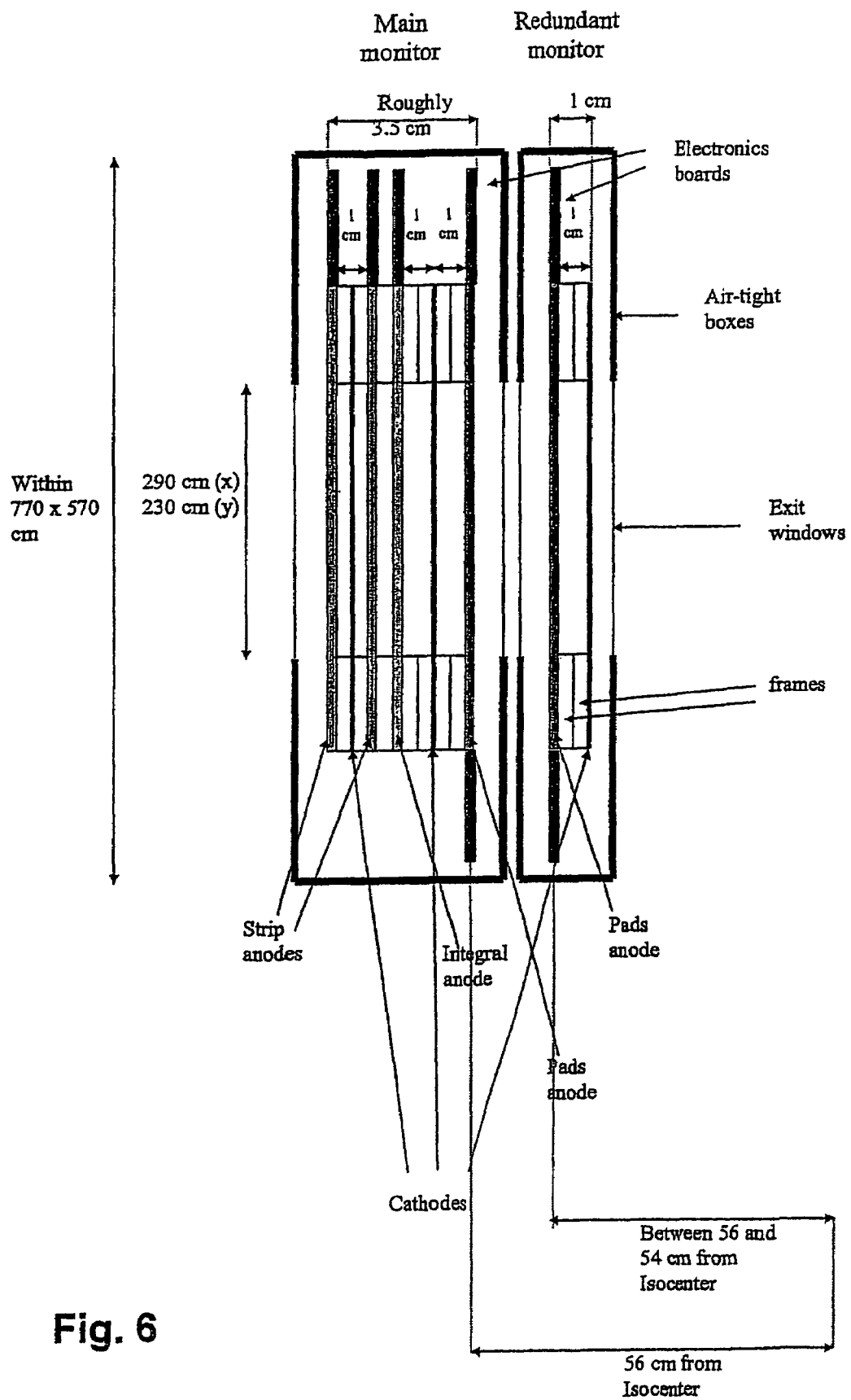
FIG. 6 is a sectional side view of a beam monitor for an irradiation apparatus according to the invention.

Referring to FIG. 6, the monitor is made of a main monitor comprising sequentially a first strip plane anode, a 5 mm gap, a dual side cathode, a 5 mm gap, a second strip plane, in an orthogonal orientation, an integral anode, a 1 cm gap, a dual side cathode, a 1 cm gap and a pad plane. The redundant monitor comprises a pad anode, a 1 cm gap and a cathode. The recycling integrator chips are located on the sides of the planes. Both chambers have a metallic enclosure and thin entrance and exit window metallic foils. The enclosures and windows are grounded. Both enclosures are filled with dry air or nitrogen.

In contrast to other beam delivery methods, like the double scattering method, in the PBS method, one can keep the beam in the vacuum tube almost up to the patient. The only equipment in line with the beam is the monitor, and this one is located at the end of a prolonged vacuum tube. The length of travel of the beam in air, which cause beam scattering, is thereby minimised. The distance between the monitor and isocenter is less than 60 cm.

The invention claimed is:

1. An irradiation apparatus for irradiating by scanning a target volume according to a predetermined dose profile with a scanning beam of charged particles forming an irradiation spot on said target volume, said apparatus comprising:
    a beam generating device,
    a reference generator for computing, from said predetermined dose profile, through a dynamic inverse control strategy, the time evolution of commanded variables, these variables being the beam current I(t), the spot position settings x(t),y(t) and the scanning speed settings $v_x(t)$, $v_y(t)$,
    a monitor device having means for detecting at each time (t), the actual spot position as a measured position defined by the values $x_m(t),y_m(t)$ on the target volume,
    wherein said irradiation apparatus further comprises means for determining the differences $e_x(t)$, $e_y(t)$ between the measured values $x_m(t)$, $y_m(t)$ and the spot position settings x(t) and y(t), and means for applying a correction to the scanning speed settings $v_x(t)$ and $v_y(t)$ depending on said differences $e_x(t)$, $e_y(t)$.

2. The irradiation apparatus according to claim 1, wherein the monitor device further comprises means for measuring the total instantaneous dose deposited by the beam in the target volume, and means for correcting this dose deposition or for pausing the beam and informing an external operator when said instantaneous dose is outside of an expected range.

3. The irradiation apparatus according to claim 1, arranged so as to generate a beam in one direction and so as to irradiate with said beam the target volume in layers perpendicular to said direction, said layers being irradiated in one or more irradiation frames, wherein the monitor device comprises in addition means for determining the dose distribution in a plane perpendicular to the beam direction, for each successive irradiation frame, and means for pausing the beam and informing an external operator when said dose distribution is outside of an expected range.

4. A process implementing the apparatus as claimed in claim 1, said process comprising the steps of:
- determining a dose distribution profile referenced as a map $D(x,y,z)$;
- determining, from said dose map, trajectories comprising spot position settings $x(t)$, $y(t)$, scanning speed settings $v_x(t)$, $v_y(t)$ and a beam current setting $I(t)$ for a set of irradiation depths z;
- feeding said scanning speed signals $v_x(t)$ and $v_y(t)$ to a scanning magnet system;
- feeding said beam current signal $I(t)$ to a beam generating device;
- detecting and measuring the actual spot values $x_m(t)$, $y_m(t)$, determining the differences $e_x(t)$, $e_y(t)$ between said measured spot values $x_m(t)$, $y_m(t)$ and the spot position settings $x(t)$ and $y(t)$; and
- applying a correction to the scanning speed settings $v_x(t)$ and $v_y(t)$ depending on said differences $e_x(t)$, $e_y(t)$.

5. Use of the apparatus according to claim 1 or a process implementing the apparatus as claimed in claim 1, said process comprising the steps of:
- determining a dose distribution profile referenced as a map $D(x,y,z)$;
- determining, from said dose map, trajectories comprising spot position settings $x(t)$, $y(t)$,
- determining, from said dose map, trajectories comprising spot position settings $x(t)$, $v(t)$, scanning speed settings $v_x(t)$, $v_y t$ and a beam current setting $I(t)$ for a set of irradiation depths z;
- feeding said scanning speed signals $v_x(t)$ and $v_y(t)$ to a scanning magnet system;
- feeding said beam current signal $I(t)$ to a beam generating device;
- detecting and measuring the actual spot values $x_m(t)$, $y_m(t)$,
- determining the differences $e_x(t)$, $e_y(t)$ between said measured spot values $x_m(t)$, $y_m(t)$ and the spot position settings $x(t)$ and $v(t)$; and
- applying a correction to the scanning speed settings $v_x(t)$ and $v_y(t)$ depending on said differences $e_x(t)$, $e_y(t)$ for irradiating a target.

* * * * *